United States Patent
Hermine et al.

(10) Patent No.: US 9,377,471 B2
(45) Date of Patent: Jun. 28, 2016

(54) METHODS AND COMPOSITIONS FOR THE TREATMENT OF β-THALASSEMIA

(71) Applicants: Institut National de la Sante et de la Recherche Medicale (INSERM), Paris (FR); CENTRE NATIONAL DE LA RECHERCHE SCIENTIFIQUE (CNRS), Paris (FR); Universite Paris Descartes—Paris V, Paris (FR); Assistance Publique—Hopitaux de Paris, Paris (FR); Fondation Imagine, Paris (FR)

(72) Inventors: Olivier Hermine, Paris (FR); Genevieve Courtois, Paris (FR); Jean-Benoit Arlet, Paris (FR); Jean-Antoine Ribeil, Paris (FR)

(73) Assignees: Institut National de la Sante et de la Recherche Medicale (INSERM), Paris (FR); CENTRE NATIONAL DE LA RECHERCHE SCIENTIFIQUE (CNRS), Paris (FR); Universite Paris Descartes—Paris V, Paris (FR); Assistance Publique—Hopitaux de Paris, Paris (FR); Fondation Imagine, Paris (FR)

( * ) Notice: Subject to any disclaimer, the term of this patent is extended or adjusted under 35 U.S.C. 154(b) by 8 days.

(21) Appl. No.: 14/547,208

(22) Filed: Nov. 19, 2014

(65) Prior Publication Data
US 2015/0141341 A1 May 21, 2015

Related U.S. Application Data

(60) Provisional application No. 61/906,556, filed on Nov. 20, 2013.

(51) Int. Cl.
 *G01N 33/68* (2006.01)
 *A61K 38/16* (2006.01)
 *G01N 33/80* (2006.01)

(52) U.S. Cl.
 CPC ............ *G01N 33/6893* (2013.01); *G01N 33/80* (2013.01); *G01N 2333/805* (2013.01); *G01N 2500/02* (2013.01); *G01N 2800/22* (2013.01)

(58) Field of Classification Search
 CPC .............................................. B01J 2219/00585
 See application file for complete search history.

(56) References Cited

PUBLICATIONS

Arlet et al., "Heat Shock Protein 70 Cytosolic Sequestration by Excess of Free Alpha-Globin Chains Is a Key Mechanism of the Ineffective Erythropoiesis in β-Thalassemia Major Patients", Blood, 54th Annual Meeting and Exposition of the American Society of Hematology, Abstract 823, Nov. 16, 2012, pp. 1-3.*
Arlet et al., "HSP70 sequestration by free alpha-globin promotes ineffective erythropoiesis in beta-thalassaemia", Nature, Aug. 24, 2014.

* cited by examiner

*Primary Examiner* — Lianko Garyu
(74) *Attorney, Agent, or Firm* — Whitham, Curtis & Cook, P.C.

(57) ABSTRACT

Methods and compositions for the treatment of β-thalassemia are provided. Methods and compositions restore or increase erythrocyte maturation in individuals afflicted with β-TM by preventing proteolysis of GATA-1 protein. Screening methods for identifying agents which bind heat shock protein 70 (HSP-70) and inhibit HSP-70 α-globin binding, but which allow GATA-1 protein-HSP-1 binding in a manner that prevents GATA-1 proteolysis.

2 Claims, 10 Drawing Sheets

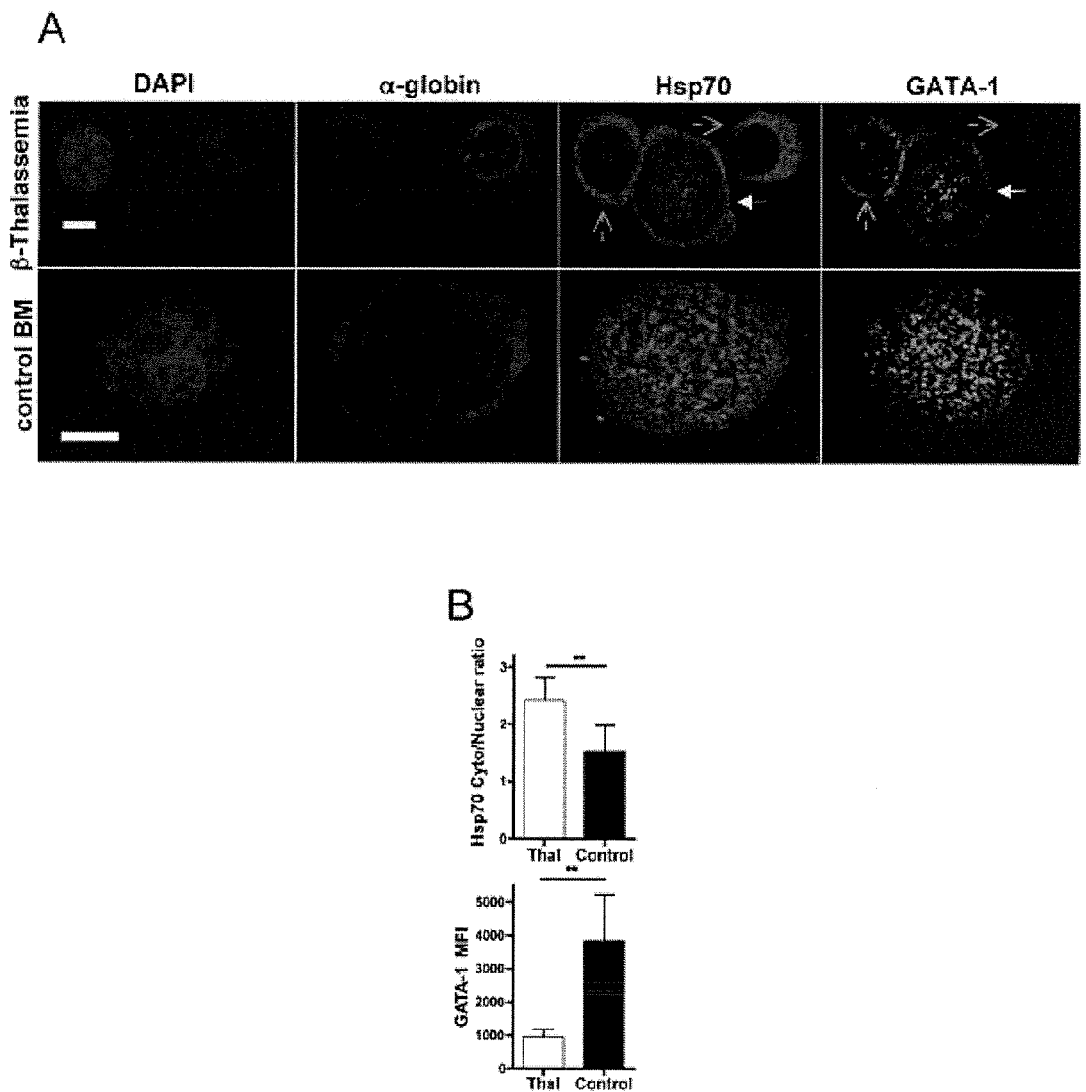
Figure 1A and B

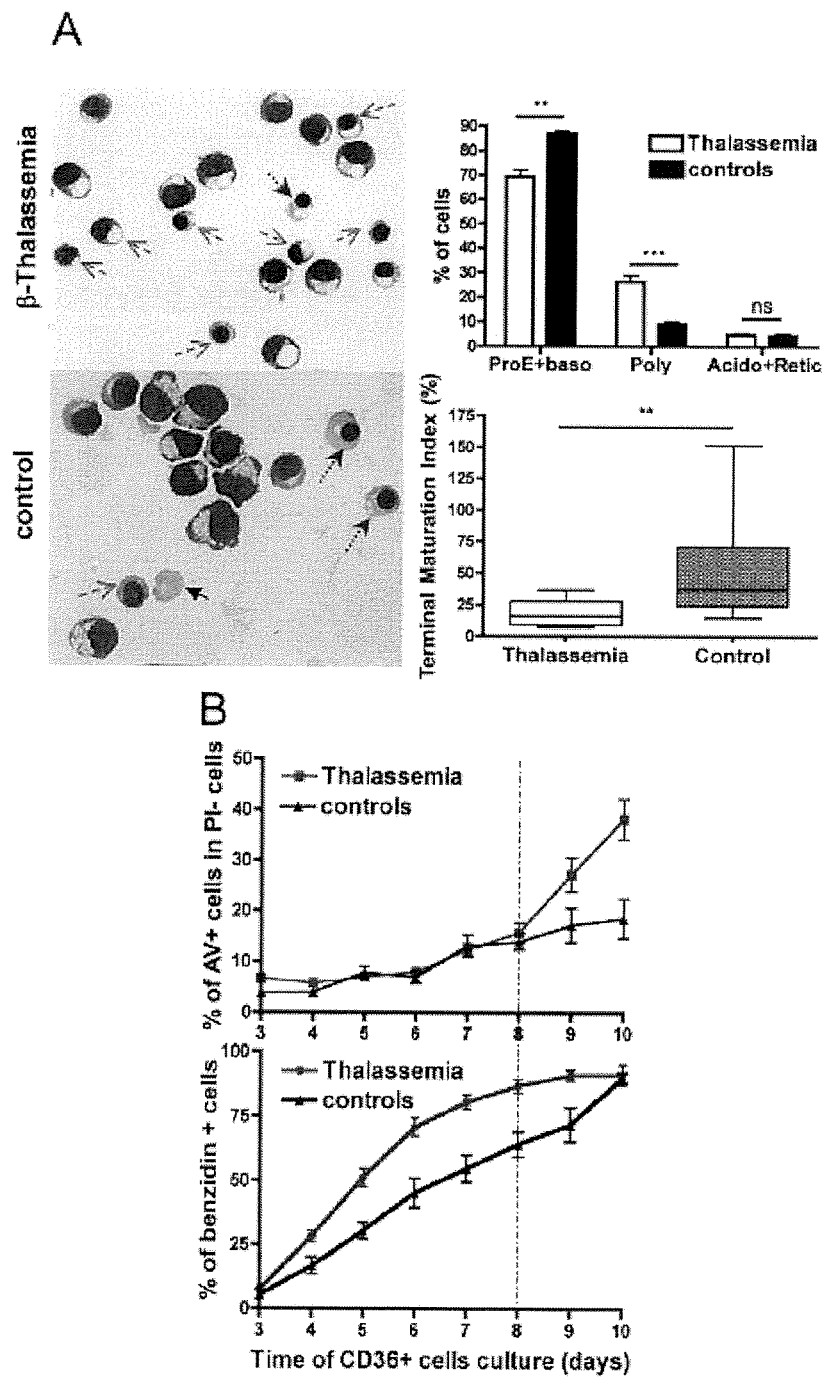
Figure 2A and B

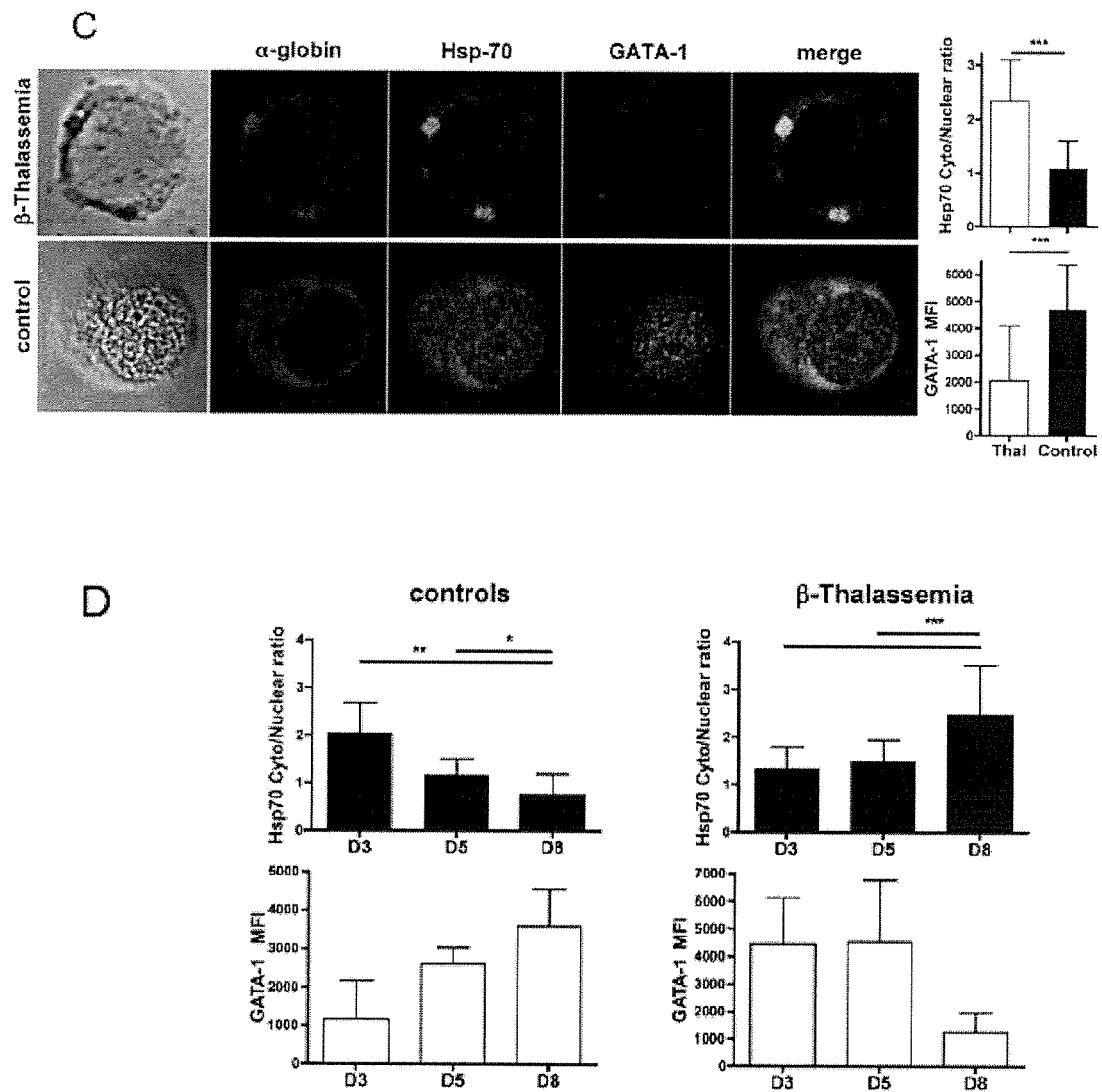
Figure 2C and D

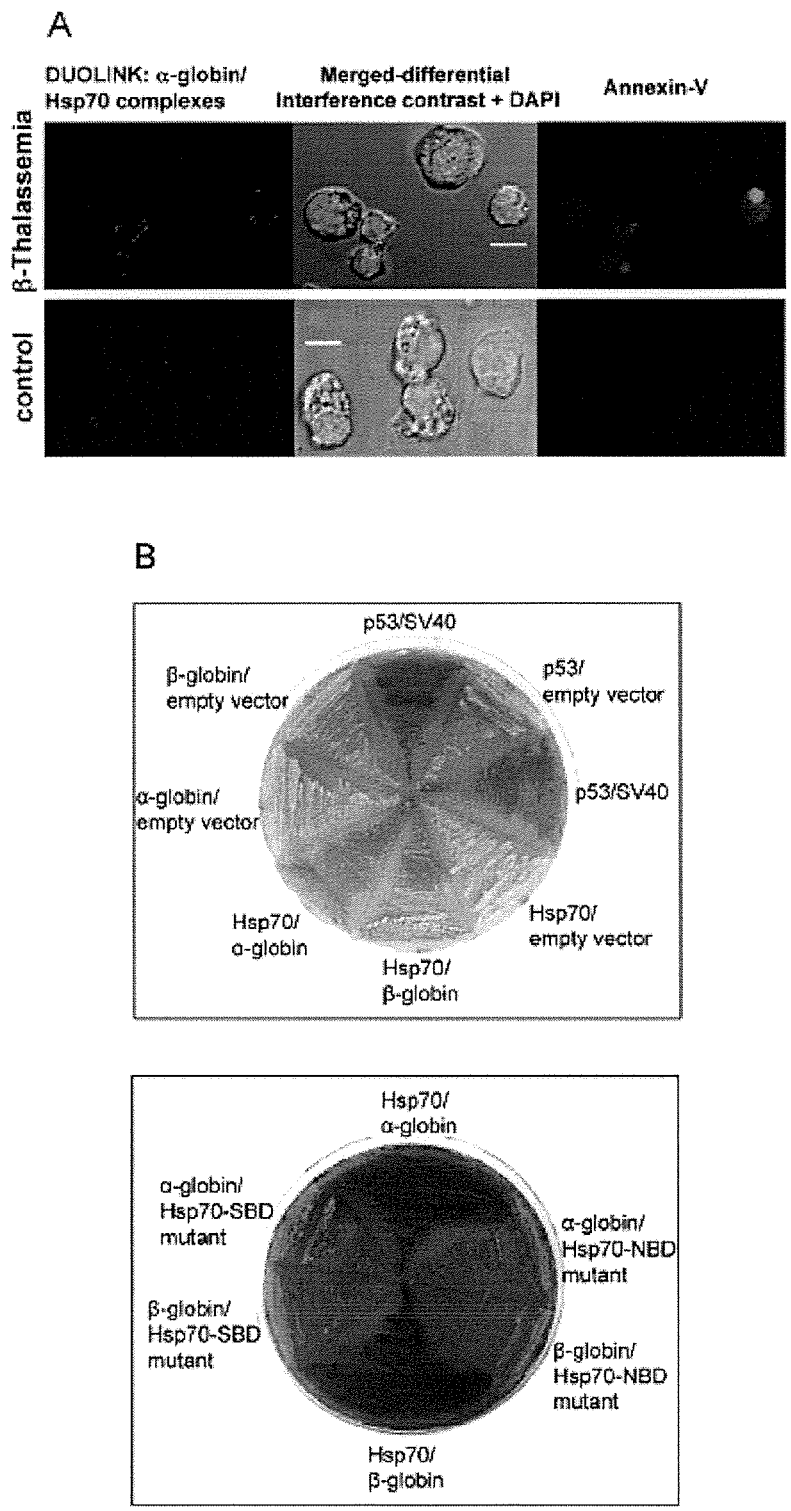
Figure 3A and B

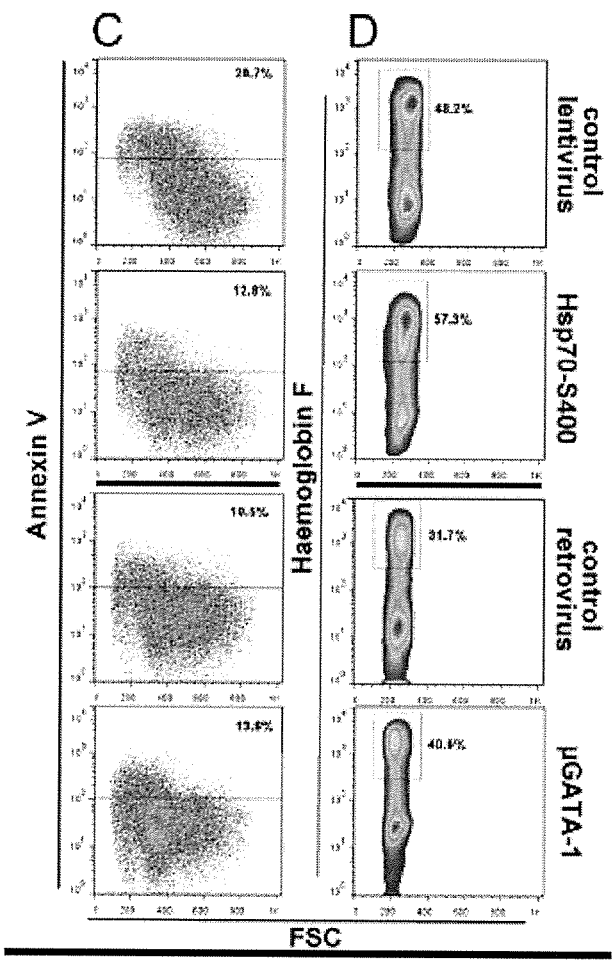
Figure 4C and D

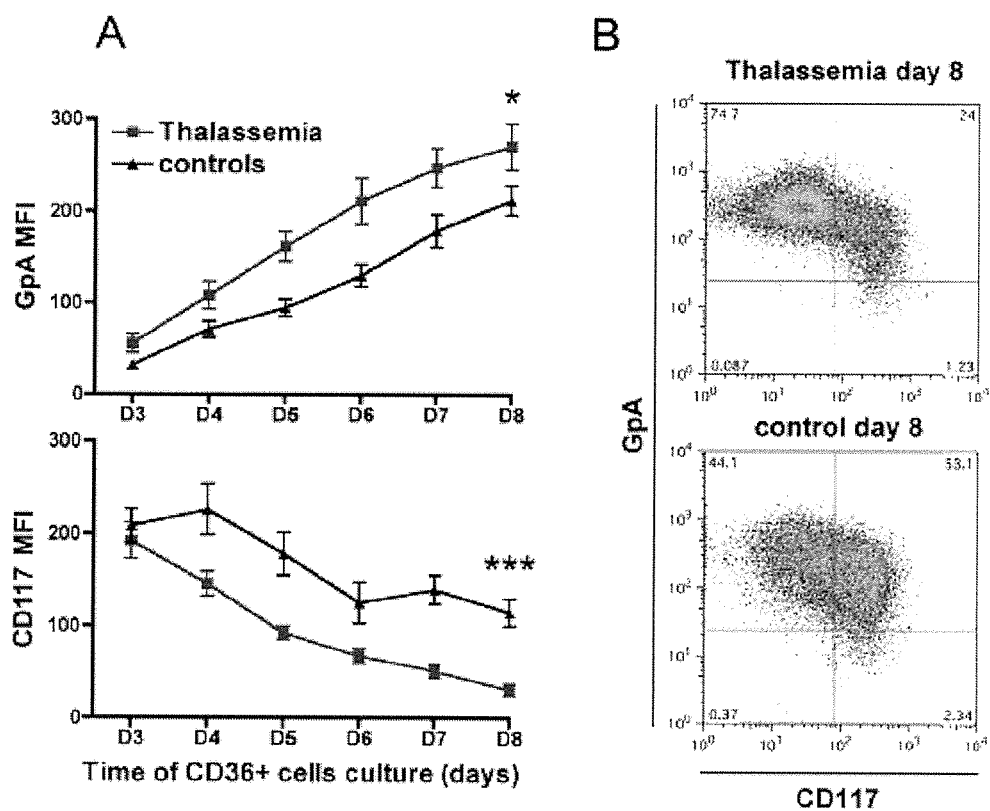
Figure 5A and B

METHODS AND COMPOSITIONS FOR THE TREATMENT OF β-THALASSEMIA

BACKGROUND OF THE INVENTION

Field of the Invention

The invention generally relates to the treatment of β-thalassemia (β-TM). In particular, the invention provides methods and compositions for restoring or increasing erythrocyte maturation in individuals afflicted with β-TM by preventing proteolysis of GATA-1 protein.

BACKGROUND OF THE INVENTION

Adult mammalian Hg is a multimeric protein that includes two α and two β globin chains which together form the $(\alpha/\beta)_2$ tetrameric hemoglobin (Hb) molecule. Beta-thalassemias are a group of inherited blood disorders caused by a quantitative defect in the synthesis of the β chains of hemoglobin. In individuals with this disorder, the synthesis of β-globin chains is reduced or absent. Three main forms of the disease have been described: β-thalassemia major β-TM or $\beta^0$-TM) in which no β chain is produced, and β-thalassemia intermedia and β-thalassemia minor, in which β chain is produced but in lower than normal amounts. These conditions cause variable phenotypes ranging from severe anemia to clinically asymptomatic individuals. Individuals with β-TM usually present within the first two years of life with severe anemia, poor growth, and skeletal abnormalities during infancy. Affected children will require regular lifelong blood transfusions. β-thalassemia intermedia is less severe than β-thalassemia major and may require episodic blood transfusions. Transfusion-dependent patients will develop iron overload and require chelation therapy to remove the excess iron.

It is known that defective β-globin chain synthesis leads to the accumulation of free α-globin chains that form toxic aggregates [1,2]. However, despite extensive knowledge on the molecular defects causing β-TM, little is known about the mechanisms responsible for ineffective erythropoiesis (IE) in β-TM patients. In such individuals, erythropoiesis does not result in the production of mature erythrocytes but instead is characterized by accelerated erythroid differentiation, maturation arrest and apoptosis at the polychromatophilic stage [3-5]. This lack of understanding of the mechanism has prevented the development of effective strategies for treating the disease.

Humans are capable of producing three types of Hb chains: α, β and γ. The main oxygen transport protein in the human fetus during the last seven months of development in the uterus and in the newborn until roughly 6 months of age is $(\alpha/\gamma)_2$ Hb. As the nomenclature indicates, this type of Hb tetramer contains two α globin subunits and two γ globin subunits. After about 6 months of age, humans shift from production of $(\alpha/\gamma)_2$ Hb toward production of $(\alpha/\beta)_2$ Hb, and in non-β-TM adult humans, $(\alpha/\gamma)_2$ Hb represents only about 1% or less of hemoglobin. However, the amount of $(\alpha/\gamma)_2$ Hb is increased in individuals with β-TM. Functionally, fetal hemoglobin differs from adult hemoglobin in that it is able to bind oxygen with greater affinity than the adult form, giving the developing fetus better access to oxygen from the mother's bloodstream. Thus, the production of $(\alpha/\gamma)_2$ by β-TM cells could, in theory, be a boon for those suffering from thalassemias. However, since β-TM erythrocytes generally fail to mature, the presence of the alternate form of Hb is not especially useful to patients with this disease.

SUMMARY OF THE INVENTION

Individuals afflicted with the genetic disease β-TM do not produce hemoglobin β chains. Thus, mature $(\alpha/\beta)_2$ Hb cannot be formed and the α globin chains that are produced accumulate in the cytoplasm of immature erythrocytes (erythroblasts). Up until the present invention, the relationship between α chain accumulation and the etiology of β-TM was unknown. The lack of knowledge greatly hampered the development of effective treatment regimes for β-TM patients.

The present inventors have elucidated the consequences of α chain cytoplasmic accumulation and the cascade of failed reactions that result therefrom which ultimately cause β-TM symptoms such as anemia. The discovery is based on the further clarification of the roles of the chaperone protein Hsp70 and the erythrocyte maturation protein GATA-1. The inventors have discovered that Hsp70 has important functions in both the cytoplasm and the nucleus of erythroblasts. A primary function of Hsp70 in the nucleus is binding to the GATA-1 protein and preventing its cleavage and proteolytic degradation (by the protease caspase-1). GATA-1 thus prevents inactivation of GATA-1 and preserves its function as a key factor in erythrocyte maturation. A secondary function of Hsp70 is binding to α globin in the cytoplasm and ensuring that the protein chains are properly folded and can form tetrameric $(\alpha/\beta)_2$ Hb. Ordinarily, there is sufficient Hsp70 available in the cell to carry out both of these functions. However, in β-TM cells, the Hsp70 is monopolized by the excess free α chains which accumulate in the cytoplasm. Thus, a disproportionate amount of the Hsp70 is sequestered in the cytoplasm, and there is not sufficient Hsp70 available for binding and protecting GATA-1 in the nucleus. Unprotected GATA-1 is proteolytically cleaved and inactivated, and proper erythrocyte maturation does not occur. Rather, the absence of active GATA-1 results in maturation arrest and apoptosis of immature erythrocytes at the polychromatophilic stage. This sequence of events is thus initially triggered by a lack of hemoglobin β chains and ultimately results in low (or no) erythrocyte production, causing anemia.

The present invention provides methods and pharmaceutical compositions designed to intervene in this defective process and to promote or restore erythrocyte maturation in individuals suffering from β-TM. It is noted that because β globin is not formed in β-TM erythrocytes, the type of erythrocytes that are produced in individuals treated with the methods and compositions described herein contain $(\alpha/\gamma)_2$ Hb, and the invention provides methods and compositions for increasing the production of $(\alpha/\gamma)_2$ Hb erythrocytes in β-TM cells and β-TM individuals. The methods involve maintaining the activity of GATA-1 by preventing its proteolysis, e.g. by preventing sequestration of Hsp70 in the cytoplasm.

Accordingly, it is an object of this invention to provide methods of restoring or increasing erythrocyte maturation in a subject suffering from β-thalassemia major (β-TM) by preventing proteolytic inactivation of GATA-1. In some embodiments, preventing is achieved by administering to the subject a compound that inhibits binding of α globin to Hsp70. In an exemplary aspect, the compound that inhibits binding of α globin to Hsp70 is a small molecule that binds to the α chain binding pocket of Hsp70. The invention also includes screening methods to identify such agents.

Other features and advantages of the present invention will be set forth in the description of invention that follows, and in part will be apparent from the description or may be learned by practice of the invention. The invention will be realized and attained by the compositions and methods particularly pointed out in the written description and claims.

BRIEF DESCRIPTION OF THE DRAWINGS

FIG. 1A-B. Hsp70 and GATA-1 expression in fresh bone marrow of β-thalassemia major patients (β-TM). (A) Representative confocal microscopy analysis of α-globin, Hsp70 and GATA-1 expression in fresh bone marrow (BM) from 3 adult β-TM patients and 3 healthy donors. Scale bar, 5 µm. Gray arrows indicate Hsp70 cytoplasmic sequestration into mature β-TM cell, and the white arrow shows immature cell. (B) Hsp70 cytoplasmic/nuclear mean fluorescence intensity (MFI) ratio (top) and GATA-1 nuclear MFI (bottom) of β-TM and controls. Bars indicate the median (IQR). p values were calculated using the Mann-Whitney U-test. **p<0.01.

FIG. 2A-D. The characteristics of ineffective erythropoiesis in β-TM and the kinetics of Hsp70 and GATA-1 expression during in vitro erythroid differentiation. $CD36^+$ cells derived from $CD34^+$ adult β-TM peripheral blood cells (n=16 independent experiments, 7 patients) or healthy peripheral blood cells (controls, n=8) were cultured with a two-phase amplification liquid culture system, as described in Methods section. Day 0 of differentiation is the start of $CD36^+$ cell culture and represents the differentiation phase of the culture system. (A) May-Grünwald-Giemsa staining at day 8. Left panel. A representative morphological analysis (×40) of erythroid differentiation is shown. Solid arrows indicate reticulocytes, dashed arrows represent acidophilic cells, and dotted arrows represent polychromatophilics cells. Upper right panel: graph represents proportion of each erythroid stage in β-TM or control-derived cells. Proerythtroblast (ProE)+basophilic (baso), polychromatophilics (Poly) cells and very mature cells-acidophilic cells (Acido)+reticulocytes (Retic) are expressed as a percentage of the total erythroid cells. Bars indicate the mean±SEM for 14 independent experiments. p values were calculated using t-tests. p<0.01; *p<0.001. Lower right panel: graph represents the terminal maturation index of β-TM and control-derived cells, as calculated by (acidophilic cells+reticulocytes per slide)×100/polychromatophilic cells per slide. The box and whiskers indicate the median extremes. p<0.01. (B) Upper: apoptosis curves assessed daily by flow cytometry analysis of Annexin-V (AV) staining (mean percentage±SEM of AV positive, Propidium Iodide (PI) negative cells). Lower: differentiation curves assessed by benzidine staining. The results are the means of 17 independent experiments (mean percentage±SEM of positive cells). (C) Left: representative confocal microscopy analysis of Hsp70, GATA-1 and α-globin at day 8. The merged panel shows Hsp70 and α-globin co-localisation in the cytoplasm. Bar graphs at the right show: upper, Hsp70 cytoplasmic/nuclear MFI ratio and; lower, nuclear GATA-1 MFI of β-TM and control-derived cells. Bars indicate the median (IQR) of 15 independent experiments. p values 15 were calculated using the Mann-Whitney U-test. *p<0.001. (D) Kinetics of Hsp70 and GATA-1 expression in vitro. Hsp70 cytoplasmic/nuclear MFI ratio and GATA-1 nuclear MFI were analysed at days 3, 5 and 8 of culture: right, 3 β-TM patients; and left, 3 controls. Bars indicate the median (IQR). p values were calculated using the Mann-Whitney U-test. *p<0.05, p<0.01; *p<0.001.

FIG. 3A-C: Hsp70 and α-globin interaction. (A) DUOLINK® in situ proximity ligation assay (PLA). Interactions were analysed at day 8 in $CD36^+$ β-TM or control-derived cell cultures by PLA, according to the manufacturer's instructions using Hsp70 (1:200) and α-globin (1:200) antibodies. A FITC-conjugated Annexin-V antibody (1:200) was added at the end of the assay. The spots indicate close proximity (<40 nm) between cellular bound antibodies. A representative experiment is shown (n=3). Nuclei are stained with DAPI, and Annexin-V staining is also shown. Scale bar, 5 µm. (B) Yeast two-hybrid assay detected, in upper panel, a direct interaction of α- and β-globin chains with Hsp70 (diploid yeast cells), but not, in lower panel, with the Hsp70 deletion mutants, Hsp70-Nucleotide Binding Domain (NBD) or Hsp70-Substrate Binding Domain (SBD). Each section contains diploid yeast cells resulting from an independent yeast mating experiment with the corresponding bait protein and prey protein. The empty vectors, pGADT7 and pGBKT7, are used as negative controls. SV40 and p53 coding sequences are used as positive controls. (C) Structural modelling of Hsp70 and the $Hsp70^{1-701}$/α-globin complex. In the upper panel, from left to right, are the molecular surface and cartoon representation of the generated models of Hsp70, the Hsp70/α-globin complex and their superimposition. The different Hsp70 domains are labelled and highlighted. The lid, the SBD, the NBD, the hinge region between the NBD and the SBD, and α-globin are shown. The superimposed models are presented in transparent (Hsp70) and contrast (Hsp70/α-globin complex) modes. The lid and SBD movements are shown by arrows. The haem group and ADP are shown by space-filling models. In the lower panel, from left to right, are the electrostatic potential of the molecular surfaces of the $Hsp70^{1-701}$/α-globin complex, where Hsp70 and α-globin are shown. The α-globin in the $Hsp70^{1-701}$/α-globin complex is shown for clarity. α-globin is rotated 180° respectively to its position in the $Hsp70^{1-701}$/α-globin complex, and its image is flipped horizontally to show the charge distribution on the surface interacting with Hsp70.

FIG. 4A-D. The transduction of a nuclear Hsp70 mutant (Hsp70-S400A) or a caspase resistant GATA-1 mutant (µGATA-1) rescues cell terminal maturation and cell survival in β-thalassemia major (β-TM). β-TM CD34+ cells were transduced with a nuclear-targeted Hsp70 lentiviral mutant (Hsp70-S400A), a retroviral mutant of GATA-1 uncleavable by activated caspase-3 (µGATA-1), and their appropriate empty vectors as controls and were cultured as described in the methods. $CD36^+/GFP^+$ cells were then purified, cultured, and differentiated in Epo-containing medium. All data presented here were analysed at day 7 of the $CD36^+$ culture. (A) A confocal microscopy image of Hsp70 and GATA-1 is shown in the left panel. The image is representative of three experiments. Graphs in the right panel represent the nuclear mean fluorescence intensity (MFI) of Hsp70 and GATA-1 (±95% CI) in transduced and control cells (top panel: Hsp70-S400A transduced cells; bottom panel: µGATA-1 transducted cells) (20 cells were analysed in three different fields/slide, n=3 patients). Scale bar, 5 µm. P values were calculated using Mann-Whitney U-test. ***p<0.001. (B) May-Grünwald-Giemsa (MGG) staining at day 7. Left panel: Graphs represent proportion of each erythroid stage in transduced and control β-TM cells (upper panel, Hsp70-S400A; lower panel, µGATA-1). Proeryhtroblast (ProE)+basophilic (baso), polychromatophilics (Poly) cells and very mature cells-acidophilic cells (Acido)+reticulocytes (Retic) are expressed as a percentage of the total erythroid cells. Bars indicate the mean±SEM for 3 independent experiments. p values were calculated using t-tests. Right panel: one representative morphological analysis of the erythroid differentiation for each transduction (n=3) is shown (×100). Solid arrows indicate reticulocytes, dashed arrows indicate acidophilic cells, and dotted arrows indicate polychromatophilic cells. (C) Apoptosis in the $GFP^+$/propidium iodide-cell population was assessed by Annexin V binding by flow cytometry. A representative experiment of each transduction is shown (n=3 patients/transduction). (D) The percentage of HbFhigh cells was assessed by flow cytometry on mature cells (GFP$^+$ and low forward light scatter-FSC). A representative experiment of each transduction is shown (n=3 patients/infection).

FIGS. 5A and B. The kinetics of differentiation of β-TM and control progenitors. CD36$^+$ cells derived from CD34$^+$β-TM peripheral blood cells (n=16 independent experiments, 7 patients) or healthy peripheral blood cells (controls, n=8) were cultured with a two-phase amplification liquid culture system, as described. Day 0 of differentiation is the 18 start of CD36$^+$ cell culture, which represents the differentiation phase of the culture system. Differentiation staining was assessed daily by flow cytometry. (A) Upper panel: differentiation curves assessed by Glycophorin A (GpA) mean fluorescence intensity (MFI). Lower panel: differentiation curves assessed by c-KIT/CD117 staining mean fluorescence intensity (MFI). The results are means (±SEM). p values compare β-TM and control-derived cells differentiated at day 8 and were calculated using t-tests. *p<0.05, ***p<0.001. (B) One representative flow cytometry image of the stage of erythroid differentiation at day 8 of culture is shown for β-TM (upper panel) and control-derived cells (lower panel). GpA$^+$/CD117$^-$ cells represent mature erythroid cells.

DETAILED DESCRIPTION

Figure 3C:
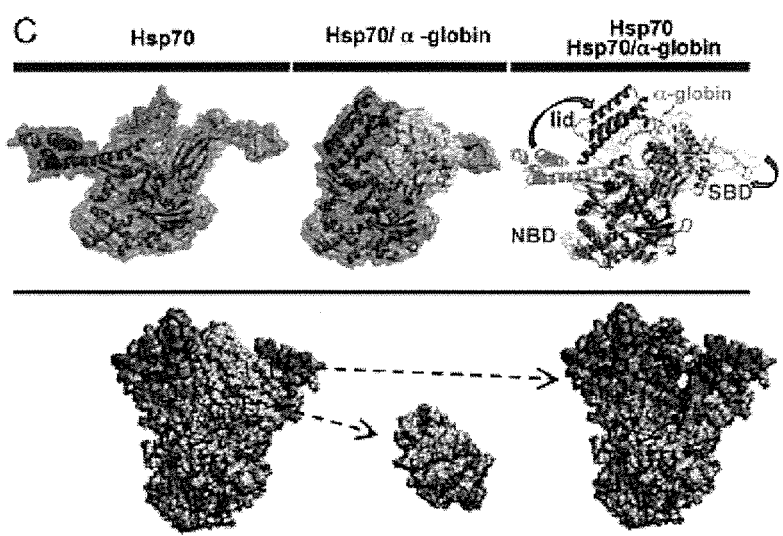

Methods and compositions for increasing erythrocyte maturation in individuals suffering from β thalassemia are provided. The methods involve preventing the otherwise untoward effects of Hsp70 sequestration in the cytoplasm of maturing erythrocytes. The invention takes advantage of the new understanding of the mechanism behind the β-TM disease process as described herein, in order to provide methods and compositions for increasing the maturation of erythrocytes containing HbF in β-TM subjects.

The inventors have found that symptoms of β-TM can be alleviated by compositions and methods which slow or prevent (e.g. interfere with, impede, stop, decrease, etc.) cleavage and inactivation of GATA-1, or conversely, which preserve or promote the erythrocyte maturation activity of GATA-1. Several avenues of doing so are provided.

In one aspect, GATA-1 inactivation is prevented by disrupting formation of the Hsp70/α globin complex in the cytoplasm, thereby increasing the concentration of Hsp70 in the nucleus of β-TM cells, increasing nuclear localization of Hsp70, reducing maturation arrest and increasing the number of HbF cells. Using both wet and in silico chemistries, the Hsp70 α globin binding site has been elucidated, and it has been surprisingly discovered that the binding site may be blocked or altered in ways that prevent α globin binding but that do not impair the ability of Hsp70 to fulfill other functions in the cell, such as protecting the GATA-1 protein from proteolysis.

Thus, in some aspects, the invention provides compositions and methods for blocking the α Hb binding site of Hsp70, without interfering significantly with the ability of Hsp70 to enter or access the nucleus, bind GATA-1 and protect it from proteolytic degradation, e.g. by caspase-1. Blockage of the α Hb binding site may be carried out by contacting Hsp70 in β-TM cells with a ligand that binds with relatively high affinity to the α globin binding site, the affinity usually being at least equal to or greater than that of α globin i.e. the Kd of the ligand is approximately equal to or lower than that of α globin. Binding of the ligand may be competitive so that α globin is outcompeted and the equilibrium distribution of Hsp70 between the cytoplasm and nucleus is shifted, and so that at least a portion of the Hsp70 that is present in the cell is not complexed to α globin in the cytoplasm. Alternatively, ligand binding may be irreversible so that Hsp70 that binds the ligand cannot bind α globin, but can still access and bind GATA-1 protein in the nucleus.

Ligands which may be used in the practice of the invention include but are not limited to various so-called "small molecules". A "small molecule" is generally a low molecular weight (<900 Daltons organic compound with a size on the order of $10^{-9}$ m. In general, the upper molecular weight limit for a small molecule is approximately 900 Daltons which allows for the possibility to rapidly diffuse across cell membranes and reach intracellular sites of action. In addition, this molecular weight cutoff is a favorable (although insufficient) condition for oral bioavailability. In some aspects, lower molecular weight compounds may be used, e.g. compounds of about 100, 200, 300, 400, 500, 600, 700 or 800 Daltons or less. The compound may, but does not always, obey "Lipinski's rule", which states that, in general, an orally active drug has no more than one violation of the following criteria:

1. Not more than 5 hydrogen bond donors (nitrogen or oxygen atoms with one or more hydrogen atoms)
2. Not more than 10 hydrogen bond acceptors (nitrogen or oxygen atoms)
3. A molecular mass less than 500 daltons
4. An octanol-water partition coefficient [5] log P not greater than 5.

Such "small molecule" drugs (active agents) are generally designed to interact with amino acid residues and/or with functional groups thereof, located in the α chain binding pocket of Hsp70. By the "α chain binding pocket" of Hsp70, we mean the highly electronegative cavity formed by the N-terminal nucleotide binding domain (NBD), the C-terminal substrate binding-domain (SBD) and the lid (a C-terminal 10 kDa helical subdomain of the SBD) of Hsp70. Suitable small molecules may be, for example, small proteins or peptides, nucleic acids, carbohydrates, antibodies, and suitable fragment thereof. Alternatively, the small molecules may be a chemically synthesized organic or inorganic molecule that is purposefully designed to fit the α chain binding pocket of Hsp70.

In further embodiments, the invention provides methods identifying compounds or agents (e.g. small molecules) that inhibit binding of α globin to Hsp70, e.g. methods of designing, generating and screening groups of agents in order to identify those which bind to, in, at or near the α chain binding pocket of Hsp70 in a manner that prevents Hsp70 from binding to α globin, or that lessens the affinity of Hsp70 for α globin. Those of skill in the art are familiar with techniques for so-called rational drug design, e.g. designing, synthesizing, and screening libraries of compounds that may have a desired activity, and then analyzing results obtained in order to select suitable ligands for use. Typically, information concerning the binding properties of the molecule to which the agent will bind is used to design, e.g. in silico, one or more suitable molecular "skeletons" or "frameworks" or "pharmacores" a possessing minimal properties required to bind to the target designed to "fit" a binding pocket, or a site adjacent to a binding pocket, or an allosteric site distant from the binding pocket but which communicates structural changes across the molecule to the binding pocket when an agent is bound thereto, etc. Various atoms or atomic groups are then added, in silico, to the basic framework in a systematic fashion, e.g. by first adding first a H atom, then a methyl group, then an ethyl group, etc. to increase the length of a variable group at one or more positions by one $CH_2$ group at a time; or a battery of positively or negatively charged groups may be placed at one or more positions, etc. Once candidate compounds or families thereof are designed in silico, various computer implemented programs can be used to identify the most likely candidates or families of molecular candidates, e.g. those which appear to possess statistically suitable binding affinities. In the present invention, such ligands must also appear to not prevent the ability of Hsp70 to bind to and protect GATA-1 from caspase-1, or at least to still allow sufficient binding to Hsp70 to GATA-1 to provide a suitable positive outcome when administered to a patient by lessening disease symptoms.

Alternatively, or in addition to (e.g. before, after or during) the process of drug design, high throughput screening (HTS) data may be used to rapidly identify active compounds of interest that bind to HSP-70. The results of HTS experiments may provide starting points for drug design, and/or confirmation of previous in silico drug design results, and/or may provide additional understanding of the interaction of HSP-70 and the candidate ligands.

Once suitable candidate ligands or families of candidate ligands are identified, synthesis of larger quantities of compounds of interest is accomplished by methods known in the art, e.g. by a suitable chemical synthetic routes. Such molecules are then tested (e.g. in vitro, in vivo using animal models, and during clinical trials) by methods known to those of skill in the art, e.g. further HTS using HSP-70 as the target, or further testing to elucidate specific attributes of the compounds (binding affinity, bioavailability, toxicity, stability, etc.).

The invention thus also provides method of screening candidate compounds in order to select compounds which inhibit binding of α globin to Hsp70 but which do not inhibit binding of Hsp70 to GATA-1. The methods may comprise, for example steps such as: i) providing a plurality of candidate compounds which may inhibit binding of α globin to Hsp70; ii) exposing Hsp70 to said plurality of candidate compounds in the presence of α globin and under conditions which allow α globin to bind to Hsp-70; iii) identifying Hsp70-compound complexes which do not contain bound α globin; iv) exposing Hsp70-compound complexes identified in said identifying step iii) to GATA-1 under conditions that permit Hsp70 to bind to GATA-1; and v) identifying Hsp70-compound-GATA-1 complexes formed in said exposing step iv); and vi) selecting compounds identified in said identifying step v) as compounds which inhibit binding of α globin to Hsp 70 but which do not inhibit binding of Hsp70 to GATA-1. The method may also comprise a step of exposing Hsp70-compound-GATA-1 complexes to caspase-1, and identifying Hsp70-compound-GATA-1 complexes in which GATA-1 is not proteolytically cleaved. In some aspects, the first exposing step may be carried out in two steps such as first exposing HSP70 to candidate compounds and identifying complexes formed between HSP70 and compounds, and then exposing the HSP70-compound complexes to α globin and selecting HSP70-compound complexes that do not bind α globin, or from which the compound is not displaced by α globin. Whatever the order of the screening steps, the compounds that are selected for clinical use (positive "hits") must interfere with or prevent or inhibit or decrease or compete with the ability of HSP70 to bind α globin, and yet not interfere with or prevent or inhibit or decrease or compete with the ability of HSP70 to bind to Hsp70-compound-GATA-1, and also confer protection from proteolysis of Hsp70-compound-GATA-1 by caspase-1. Those of skill in the art are familiar with various statistical tools that can be used to assess the significance of such data, compared to that obtained with suitable controls.

Steps of the screening method (e.g. identifying, selecting) may be carried out by attaching to or incorporating into one or more of the substances being tested (e.g. HSP-70 and/or α globin and/or the compound being tested and/or GATA-1 protein) a detectable label including but not limited to: a radioactive moiety; a bioluminescent, chemiluminescent or fluorescent label; an affinity label or tag; etc. Further, one or more of the substances may be immobilized on a substrate such as a plate or bead and the screening assays may include suitable steps of washing to remove unreacted substances, separation via size exclusion or affinity chromatography or by filtering, centrifugation, etc. Characterization of identified complexes of interest or confirmation of the identity may be carried out by known techniques, e.g. sequencing, reaction with antibodies, mass spec, etc.

The steps of the screening assays are carried out using suitable concentrations of each reactant. Viable candidates for further testing and for clinical use will typically have binding affinities (Kd values) for HSP-70 in the range of at least about 25%, and usually 30, 35, 40, 45, 50, 55, 60, 65, 70, 75, 80, 85, 90, 95% or more of that of α globin, compared to a suitable control, and the binding affinity may equal or exceed that of α globin. When bound to HSP-70, a selected compound will typically reduce the binding of α globin to HSP-70 by at least about 25%, and usually by 30, 35, 40, 45, 50, 55, 60, 65, 70, 75, 80, 85, 90, 95% or more, compared to a suitable control, and binding to may be completely prevented. When bound to an HSP-70-compound complex, GATA-1 will typically be protected so as to reduce proteolysis by at least 25%, and usually by 30, 35, 40, 45, 50, 55, 60, 65, 70, 75, 80, 85, 90, 95% or more, compared to a suitable control, and the binding of α globin to HSP-70 may be completely prevented.

The present invention provides compositions for use in methods of increasing erythrocyte maturation in individuals or subjects in need thereof, particularly those with β-TM. The compositions include one or more substantially purified active agents that promote erythrocyte maturation as described herein, and a pharmacologically suitable carrier. The preparation of such compositions for administration to a mammal is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of active agent in the formulations may vary. However, in general, the amount in the formulations will be from about 1-99%.

The active agent compositions (preparations) of the invention may be administered by any of the many suitable means which are well known to those of skill in the art, including but not limited to: by injection, (e.g. intravenous [IV], intraperitoneal, intramuscular, subcutaneous), by inhalation, orally, intravaginally, intranasally, by ingestion of a food or probiotic product containing the agent, etc. In preferred embodiments, the mode of administration is orally or by injection or IV. In addition, the compositions may be administered in conjunction with other treatment modalities such as various chemotherapeutic agents, iron supplements, blood transfusions, agents that activate γ chain expression (e.g. that cause or promote transcription or translation of Hb γ chain), and the like.

For administration of genes encoding one or more (at least one) active agent(s) as described herein, various options may be implemented. In some asepcts, nucleic acids comprising sequences encoding an active agent of the invention or functional derivatives thereof, are administered to prevent, manage, treat and/or ameliorate β thalassemia by way of gene therapy. Gene therapy refers to therapy performed by the administration to a subject of an expressed or expressible nucleic acid which encodes the active agent. Generally, the encoding region is operably linked to one or more expression control sequences, e.g. promoters, enhancers, etc. The sequence may be linked to other sequences such as STOP codons, and the like, in order to enable transcription of the gene into funcation mRNA, or, if RNA is administered, to enable translation thereof into an active form (or possibly a precursor of an active form) of the active agent. The active agent, once fully expressed, mediates a prophylactic or therapeutic effect.

Any of the methods for gene therapy available in the art can be used according to the present invention. Exemplary methods are described below. For general review of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In some embodiments, a composition of the invention comprises nucleic acids encoding an active agent of the invention, said nucleic acids being part of an expression vector that expresses the active agent in the host to whom it is administered. In particular, such nucleic acids have promoters, e.g. heterologous promoters, operably linked to the coding region, the promoter being inducible or constitutive, and, optionally, tissue- or cell-specific. In other embodiments, nucleic acid molecules are used in which the coding sequences and any other desired sequences are flanked by regions that promote homologous recombination at a desired site in the genome, thus providing for intrachromosomal expression of the antibody encoding nucleic acids (Koller and Smithies, 1989, Proc. Natl. Acad. Sci. USA 86:8932-8935; Zijlstra et al., 1989, Nature 342:435-438).

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In some embodiments, the nucleic acid sequences are administered in vivo, where the sequences are expressed to produce the encoded product. This can be accomplished by any of numerous methods known in the art, e.g., by constructing them as part of an appropriate nucleic acid expression vector and administering the vector so that the sequences become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In other embodiments, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO 92/20316; WO93/14188, WO 93/20221). Alternatively, the nucleic acid can be introduced intracellularly and incorporated within host cell DNA for expression, by homologous recombination (Koller and Smithies, 1989, Proc. Natl. Acad. Sci. USA 86:8932-8935; and Zijlstra et al., 1989, Nature 342:435-438).

In some embodiments, viral vectors that contain nucleic acid sequences encoding an active agent of the invention are used. For example, a retroviral vector can be used (see Miller et al., 1993, Meth. Enzymol. 217:581-599). These retroviral vectors contain the components necessary for the correct packaging of the viral genome and integration into the host cell DNA. The nucleic acid sequences encoding the active agent to be used in gene therapy can be cloned into one or more vectors, thereby facilitating delivery of the gene into a subject. More detail about retroviral vectors can be found in Boesen et al., 1994, Biotherapy 6:291-302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Klein et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang et al., 1995, Gene Therapy 2:775-783. In a preferred embodiment, adenovirus vectors are used. Adeno-associated virus (AAV) has also been proposed for use in gene therapy (Walsh et al., 1993, Proc. Soc. Exp. Biol. Med. 204:289-300; and U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject. In the present invention, such cells may be erythrocyles, e.g. immature erythroblasts. In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcellmediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Clin. Pharma. Ther. 29:69-92 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny. The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. In a preferred embodiment, the cell used for gene therapy is autologous to the subject.

In an embodiment in which recombinant cells are used in gene therapy, nucleic acid sequences encoding an active agent of the invention are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598; Stemple and Anderson, 1992, Cell 71:973-985; Rheinwald, 1980, Meth. Cell Bio. 21A:229; and Pittelkow and Scott, 1986, Mayo Clinic Proc. 61:771).

In some embodiments, the nucleic acid to be introduced for purposes of gene therapy comprises an inducible promoter operably linked to the coding region, such that expression of the nucleic acid is controllable by controlling the presence or absence of the appropriate inducer of transcription.

In other embodiments, the active agent of the invention is not a translatable peptide or protein but is e.g. an organic molecule that is designed and synthesized in a manner that confers on the molecule the features that are necessary or desirable to promote its interaction with and binding to the negatively charged α chain binding pocket/cleft as described herein. Methods of synthesizing molecules with e.g. charged surface atoms and/or surface atoms capable of hydrogen bonding are known. For example, various condensation reactions are used to join functional groups of interest, with or without the use of protecting groups, and in the presence of suitable solvents, to generate linked functional groups presenting desired atoms or groups of atoms in a desired location in the molecule. The molecules can be designed to include areas of rigidity and/or flexibility to accommodate the binding pocket. Positioning and spacing of the atoms is such that the groups or atoms with which they are intended to interact in binding pocket will be contacted, or at least presented within bonding distance, when introduced into the binding pocket. Typically, at least 2, and usually more (e.g. 3, 4, 5, 6, 7, 8, 9, 10 or more, e.g. 15, 20, 25, 30 or more) specific binding interactions are planned, e.g. one positively charged group to interact with one formal negative charge in the targeted binding site, 1-3 hydrogen bond donors to interact with 1-3 other hydrogen bond donors, etc. Suitable dimensions or ranges of dimensions are generally determined in silico. Candidate active agents can be manufactured and screened for activity using known methodology, e.g. via high throughput screening.

In some embodiments, the active agent is a small molecule that is a peptidomimetic. Peptidomimetic are small proteinlike chains designed to mimic a peptide of interest. For the present invention, a peptide of interest is generally α globin or a portion thereof, e.g. the portion of α globin that contacts and mediates binding to Hsp70. Peptidomimetics typically arise either from modification of an existing peptide, or by designing similar systems that mimic peptides, such as peptoids and β-peptides. Irrespective of the approach, the altered chemical structure is designed to advantageously adjust desirable molecular properties such as stability, biological activity, ligand binding, etc. The modifications generally involve changes to the peptide sequence that do not occur naturally, e.g. altered backbones, reduced peptide bonds, acylation of reactive groups, amidation of reactive groups, incorporation of normatural (non-proteinogenic or non-standard) amino acids (e.g. D-amino acids, norleucine, lanthionine, 2-aminoisobutyric acid, dehydroalanine, gamma-aminobutyric acid. ornithine, citrulline, beta alanine (3-aminopropanoic acid), carnitine, hydroxyproline, selenomethionine, homocysteine, homoserine, and homophenyalanine, S-benzyl cysteine, etc. In addition, modifications such as sulfoniation, phosphorylation, etc. may be used to create the desired binding motif.

Herein, where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

EXAMPLES

Example 1

Cytoplasmic Sequestration of Hsp70 by Excess of Free α-Globin Promotes Ineffective Erythropoiesis in β-Thalassimia It has been previously demonstrated that normal human erythroid cell maturation requires a transient activation of caspase-36. Although GATA-1, the master transcriptional factor of erythropoiesis, is a caspase-3 target, it has been shown that during human erythroid differentiation, it is protected from cleavage through its association with the chaperone heat shock protein 70 (Hsp70) in the nucleus[7]. Hsp70 is constitutively highly expressed in normal human erythroid cells[7]. The best-known role of this ubiquitous chaperone is to participate in proteins folding and refolding of proteins denatured by cytoplasmic stress, thus preventing their aggregation[8]. Here, evidence is provided showing that during the maturation of human β-TM erythroblasts, Hsp70 is sequestrated in the cytoplasm by the excess of free α-globin chains, resulting in nuclear GATA-1 cleavage and, in turn, end-stage maturation arrest and apoptosis. A molecular modelling shows that α-globin binds to a highly electronegative cavity formed by all Hsp70 domains. Additionally, the transduction of a nuclear-targeted Hsp70 mutant (Hsp70-S400A) or caspase-3 uncleavable GATA-1 mutant (µGATA-1) corrects β-thalassemia major IE in human cultured β-TM cells.

Methods

Erythroid cells were generated in vitro from the peripheral blood circulating CD34$^+$ cells from 7 adult patients with β$^0$-TM or 8 healthy donors. Fresh normal bone marrow cell smears were obtained from 3 adult patients with β$^0$-TM who had undergone cholecystectomy or splenectomy, or 3 healthy controls (allogenic bone marrow donors), after they had given written informed consent. This study was performed according to the Helsinki Declaration with the approval from the ethics committee of our institution. Erythroid cells in culture were generated as previously described [6,7]. Statistical analyses were performed using GraphPad PRIAM™ software. Data are expressed as the mean±standard deviation (SD) or median (interquartile range-IQR), unless noted otherwise. Student's paired t-test or Mann-Whitney Utest was used as appropriate. * p value <0.05,  p value <0.01, * p value <0.001

Erythroid Liquid Culture

The circulating peripheral blood of β-TM patients contains a small number of hematopoietic progenitor cells[19]. Erythroid cells were also generated in vitro from peripheral blood circulating CD34$^+$ cells from adult patients with β$^0$ thalassemia major (β-TM), which were collected before routine transfusion, or from control patients who were healthy donors treated with G-CSF to induce hematopoietic stem cell mobilisation. This study was done according to the Helsinki Declaration with the approval from the ethics committee of the Comité de Protection des personnes (CPP) "Ile de France II". All patients gave written informed consent. In the first step of culture ("cell expansion"), isolated CD34$^+$ progenitors (Miltenyi CD34 Progenitor Cell Isolation Kit) were grown in the presence of 100 ng/ml IL-6, 10 ng/ml IL-3 and 100 ng/ml SCF for 7 days. At day 7, CD36$^+$ erythroid progenitors were isolated by magnetic isolation (Miltenyi Biotec). In the second phase of culture, which allows the "differentiation and maturation of erythroblasts", CD36$^+$ cells were cultured in the presence of 10 ng/ml IL-3, 100 ng/ml SCF and 2 U/ml Epo in IMDM (Gibco cell culture) supplemented with 15% BIT 9500 (Stem Cell Technologies), as previously described [6,7].

Apoptosis Assay and Cell Differentiation

Apoptosis was assessed by Annexin V binding and propidium iodide (PI) staining (ebioscience). Early apoptotic cells were defined as Annexin-V positive and PI negative. Differentiation was assessed by various methods. First, morphological analysis after May-Grünwald-Giemsa (MGG) staining was used. Cells were examined under a Leica DMRB microscope with a PLFluotar 40× oil objective in a blinded fashion. The number of proerythroblasts, basophilic, polychromatic, acidophilic erythroblasts and reticulocytes was assessed in each experiment by counting approximately 300 cells in consecutive oil immersion fields and expressed as a percentage of total cells. Additionally, differentiation was assessed by calculating a terminal maturation index on MGG, defined by the number of acidophils+reticulocytes per slide× 100/number of polychromatophilic cells per slide. This allowed better characterization of maturation arrest at the polychromatophilic stage, which is known to be a hallmark of ineffective erythropoiesis [4], and its modulation. Haemoglobin content was also measured, as assessed by benzidine staining. Flow cytometry analysis was also performed each day after double labelling with a phycoerythrin (PE)-conjugated anti-GPA (BD Pharmingen) antibody and an APC-conjugated anti-CD117 (c-kit) (e-bioscience) antibody. The percentage of GPA+/CD117-cells represented mature erythroid cells[20]. F cells were evidenced by flow cytometry analysis. The cultured cells were fixed and permeabilised, washed with 1×PBS/1% BSA and then stained with PE-conjugated anti-human haemoglobin F (HbF) (BD Pharmingen) for 30 min at room temperature. The cells were then analysed by fluorescence-activated cell sorting (FACS).

Analysis of the Hsp70/Alpha-Globin Complex

Yeast Two-Hybrid Assay

The bait vector used was pGBKT7, and the prey vector was pGADT7 (Clontech). The human α- and β-globin coding sequences were cloned into the EcoRI/BamHI and NdeI/ClaI sites, respectively, of the pGADT7. The coding sequence of the human Heat Shock Protein 70 (Hsp70) was cloned into the EcoRI/BamHI sites of the pGBKT7. An N-terminal nucleotide binding domain (NBD) (residues 1-380) and a C-terminal substrate binding-domain (SBD) (residues 394-615) were cloned in pGBKT7. The pGBKT7-p53 plasmid was used as a positive bait control. This plasmid encodes the GAL4 DNA-BD fused with murine p53. As a positive control prey plasmid, pGADT7-SV40, which encodes the GAL4 activation domain fused with SV4021 large T-antigen, was used. The empty vector, pGADT7, was used as a negative control prey plasmid. All pGADT7- and pGBKT7-derived vectors were transformed into Y187 and Y2HGold yeast strains, respectively (Clontech Yeastmaker Yeast Transformation System 2). After growth at 30° C. for 3 to 5 days, the transformants were selected on Leu_and Trp_minimal media plates, respectively. Each prey strain was mated with the bait strain to generate diploid yeast cells (Clontech Matchmaker Gold Yeast 2-Hybrid system). Diploid yeast cells selected on Leu_Trp_minimal media plates were then patched onto Leu_Trp_minimal media plates with X-α-Galactosidase (40 μg/mL) and Aureobasidin A (70 ng/mL). Blue diploid cells appeared after 3 to 5 days at 30° C., indicating the interaction between the bait and the prey proteins. To confirm these results, the diploid yeast cells were then patched onto higher stringency His_Ade_Leu_Trp_minimal media plates supplemented with 40 μg/mL X-α-Galactosidase and 70 ng/mL Aureobasidin A.

Confocal Analysis

Cell Permeabilisation and Labelling for Fluorescence Microscopy.

The cells were washed, spun onto slides, fixed with acetone, hydrated with cold 1×PBS/1% BSA for 30 minutes, treated with formaldehyde (Sigma) for 15 minutes, and then with methanol (Prolabo) for 10 minutes at room temperature. Next, the cells were permeabilised with 1×PBS/0.2% Triton X100 (Sigma) for 10 minutes at 4° C., washed with 1×PBS/1% BSA and incubated in 3% BSA for 30 min. They were then sequentially incubated with the antibodies as follows: anti-GATA-1 overnight at 4° C., anti-rat-Cy3 for 45 minutes at room temperature, rabbit anti-Hsp70 or anti-caspase-3 for 1 hour at room temperature, anti-rabbit Alexa 647 for 45 minutes at room temperature and anti-haemoglobin-FITC (Abcam) for 60 minutes at room temperature. All antibodies were diluted in 1×PBS/1% BSA/0.1% Tween (Sigma). Nuclei were stained with DAPI, and the slides were examined with a confocal laser microscope (LSM 510 Carl Zeiss). Fresh, normal, bone-marrow cell smears were fixed with acetone. Permeabilisation and labeling with anti-GATA-1, anti-Hsp70 and anti-α globin antibodies were performed as above. To more precisely analyse the Hsp70/α-globin interaction, the Duolink® II technology (Olink® Bioscience), which is an in situ proximity ligation assay technology, was used. In this assay, a pair of secondary antibodies labelled with oligonucleotides (PLA probes) only generates a signal when the two probes are bound in close proximity (<40 nm). The signal from each detected pair of PLA probes is visualised as an individual fluorescent spot[21]. Slides were incubated with primary antibodies as described above and with secondary antibodies conjugated with oligonucleotides (PLA probe MINUS anti-mouse and PLA probe PLUS anti-rabbit). Ligation and amplification reactions were performed according to the manufacturer's instructions.

Molecular Modelling, Docking and Molecular Dynamics (MD) Simulations

All calculations were carried out on a PC station and on the Meso Center of ENS de Cachan running Linux CentOs 5.2. Figures were produced with the PyMOL molecular graphics system22, and R was used for statistical computing[23]. The template structures for homology modelling were retrieved from the Protein Data Bank (PDB)24.

Molecular Modelling

Hsp70: The 3D model of the full-length human $Hsp70^{1-701}$ was generated from partial structures (X-ray or RMN) by homology modelling of the separate Hsp70 domains and molecular complex Hsp110•Hsp70 (PDB codes: 3C7N 25, 2QWL 26, 3FE1 27 and 2LMG 28). The sequence of $Hsp70^{1-701}$ was aligned to the template sequences with ClustalW29 and Modeller30. The interdomain linkers were constructed by ab-initio loop generation using Modeler.[23]

α-globin: The initial structural data of α-globin was taken from the X-ray structure (PDB code: 3S66 31) and was docked onto the generated model of $Hsp70^{1-701}$ using three algorithms: Zdock32, FlexDock33 and HingeProt34. The minimised structure (CHARMM)35 of the $Hsp70^{1-701}$/α-globin complex was analysed for hydrophobic and electrostatic complementarities and Hbond interactions on the interface of the proteins. The $ADP-Mg^{2+}$ and $Haem Fe^{2+}$ were incorporated into proteins.

Molecular Dynamics (MD) Simulations

Molecular Dynamics (MD) simulations were performed using GROMACS 4.5.4 36 with CHARMM 27 force field. Each generated model, Hsp70 or the $Hsp70^{1-701}$/α-globin complex, was solvated in a TIP3P water box with a minimum distance of 15 Å from the edge of the box to any protein atom. The charges of the system were neutralised by adding counterions ($Na^+$ or $Cl^-$). The solvated systems were first minimised for 1,000 steps with the protein atoms restrained, followed by another 3,000 steps of minimisation with all atoms allowed to move. The temperature of each system was then increased to 300 K by increments of 0.001 K during 2 ps. The system was further equilibrated under constant volume and temperature (NRT) conditions for 100 ps constraining protein backbone atoms, followed by 500 ps equilibration without constraints under constant pressure and temperature (NPT) at 300 K and 1 bar. Production simulations were performed for 20 ns in the NPT ensemble. Short-range interactions employed a switch function with a 12 Å cut-off and a 10 Å switch distance, and the long-range electrostatic interactions were calculated with the Particle Mesh Ewald protocol37. During production simulations, the time step was 2 fs, with a SHAKE constraint on all bonds containing hydrogen atoms.

Viral Transduction

Lentiviral Production

The nucleus-targeted Hsp70 mutant (Hsp70-S400A) was cloned in the pTrip_U3EF1 lentiviral vector upstream of an IRESECMV-Green Fluorescent Protein (GFP) cassette. Infectious vector particles were produced in 293T cells by cotransfection of the vector with the encapsidation plasmid psPAX2 and the expression plasmid pHCMV-G, using the JetPRIME™ transfection reagent (Polyplus). Supernatants were collected 48 hours and 72 hours after transfection and were pooled and concentrated by ultracentrifugation. Virus stocks were kept frozen at −80° C. For the lentivirus production of the β-globin gene, vesicular stomatitis virus glycoprotein pseudotyped lentiviral supernatant was produced by transient transfection of HEK293T cells with the 5-plasmid system (LentiGlobin construct, HPV 275-gag-pol plasmid, ΨN 15-vsvG env plasmid, p633-rev plasmid, HPV601-tat plasmid) by calcium phosphate coprecipitation in Dulbecco's modified Eagle's media supplemented with 5% foetal bovine serum (Invitrogen), followed by harvest in CellGro SCGM serum-free media (CellGenix) after 48 h. Concentrated virus was then frozen and stored at −80° C.

Retroviral Production

Uncleavable mutant GATA-1 (μGATA-1) was cloned in P1NCO vector upstream of a CMV promoter-Green Fluorescent Protein (GFP) cassette. These were used to produce vector particles by cotransfection of 293EBNA cells with the vector plasmid, an encapsidation plasmid (gag-pol) lacking all accessory HIV-1 proteins, and an expression plasmid (pH-CMV-G) encoding the vesicular stomatitis virus (VSVg) envelope, using JetPRIME™ transfection reagent.

Infection of Erythroid Cells

Hsp70-S400A and μGATA-1 transduction: CD34+ cells isolated from β-TM peripheral blood mononuclear cells were cultured for 5 days, as described above. They were then infected by lentiviruses or retroviruses, in the presence of 4 μg/ml protamine sulphate. A second round of infection was performed 24 hours later, upon changing to fresh medium with cytokines. After an additional 24 hours, cells were extensively washed in PBS and stained with the anti-CD36-APC mAb (BD Pharmingen). The CD36$^+$/GFP$^+$ cell population was purified by cell sorting and cultured for 7 to 10 additional days in serum-free medium in the presence of IL3$^+$SCF$^+$EPO, as described above.

β-Globin Gene Lentivirus Transduction:

CD34$^+$ cells were isolated from β-TM peripheral blood mononuclear cells by magnetic sorting (Miltenyi Biotec). Sorted cells were prestimulated for 24 h in CellGro SCGM media supplemented with 100 ng/mL hSCF, 100 ng/mL hTPO, 100 ng/mL hFlt3L and 60 ng/mL hIL-3 at 37° C. and 5% CO2. Then, prestimulated cells were transduced for 22 h with the LentiGlobin vector at an MOI of 50 in CellGro SCGM media supplemented with 100 ng/mL hSCF, 100 ng/mL hTPO, 100 ng/mL hFlt3L, 60 ng/mL hIL-3 and 4 μg/mL protamine sulphate, or mock transduced in the same conditions. Two-phase liquid culture was then performed as described above.

Statistical Analyses

Statistical analyses were performed with GraphPad Prism™ (version 5.0; GraphPad Software). The data are expressed as the mean±standard deviation (SD) or median (interquartile range—IQR), unless noted otherwise. Student's paired t-test or Mann-Whitney U-test was used as appropriate. *p value <0.05, p value <0.01, *p value <0.001

Results

To investigate the hypothesis that Hsp70 can be sequestrated in the cytoplasm of mature β-TM erythroblasts by binding to free α-globin chains of haemoglobin or aggregates, its subcellular localisation was analyzed in fresh bone marrow samples from adult TM patients (n=3) and healthy donors (n=3) by confocal microscopy. Erythroid maturation was evaluated by cell size and by α-globin staining intensity. The results showed that Hsp70 was mainly localised in the cytoplasm and that GATA-1 was poorly expressed in the nucleus of mature haemoglobinised erythroblasts from β-TM patients, in contrast to controls (FIG. 1A).

Next, to decipher the role of Hsp70 in ineffective erythropoiesis in β-TM, an in vitro two-phase amplification liquid culture was performed, allowing the proliferation, survival and erythroid differentiation of β-TM (n=16) or control CD34+ (n=8) progenitors towards the formation of acidophilic erythroblasts and reticulocytes. During the first phase of amplification, cell proliferation did not differ between thalassemic and control cells. In contrast, during the second phase, corresponding to erythroid terminal differentiation and maturation, at day 8, we observed, in β-TM, an accelerated differentiation characterised by a higher percentage of polychromatophilic cells (26.2%±8.4 vs. 9.0%±2.7; p=0.003) (FIG. 2A), an accelerated down regulation of the early erythroid marker KIT/CD117 (mean fluorescence intensity (MFI) 25.7±17 vs. 115.1±47.1; p=0.0001) and an up regulation of GPA (MFI 243.8±87.8 vs. 178.9±56, p=0.04) (FIGS. 5A and B). At the time of intense haemoglobinisation (d8-d10), in β-TM cells, apoptosis was increased (at d10, 38.2%±15.1 vs 18.5%±8.7; p=0.01) (FIG. 2B) and terminal maturation was arrested at the polychromatophilic stage. To quantify this maturation arrest, an index of terminal maturation was defined as the number of (acidophilic cells+reticulocytes per slide)×100/number of polychromatophilic cells per slide. At day 8, this index was significantly decreased in β-TM cells, to 16% (IQR 8.8-27.8) compared to 37.6% in control cells (IQR 24.4-70.7; p=0.009) (FIG. 2A). Taken together, this system of cell culture reproduced the characteristics of IE observed in β-TM, namely accelerated differentiation, maturation arrest and the death of mature haemoglobinised cells [3-5]. Next, the subcellular localisation of Hsp70 was analysed at several time intervals in β-TM patients (n=7) and healthy donors (n=7) by confocal microscopy. In agreement with what we observed in fresh primary bone marrow erythroblasts, Hsp70 was detected in the nucleus of control cells but was absent or only weakly expressed in mature haemoglobinised β-TM cells. Thus, at day 8, the ratio of cytosoplasmic/nuclear Hsp70 MFI in β-TM erythroblast cells was significantly increased, with a median ratio of 2.3 (IQR 1.6-3) compared to 1.1 in control cells (IQR 0.7-1.6; p<0.0001) (FIG. 2C). As a result, GATA-1 was poorly expressed in the nucleus of mature haemoglobinised β-TM erythroblasts (FIG. 2C), thus supporting the hypothesis. To further analyse and understand the link between haemoglobinisation, Hsp70 localisation and the decrease in GATA-1 expression, the changes in the expression of these proteins during differentiation and maturation was studied. In β-TM derived cells, the intensity of nuclear Hsp70 and GATA-1 staining decreased with erythroid differentiation and maturation, while these increased in controls (FIG. 2D).

To demonstrate that Hsp70 could act as a molecular chaperone of free α-globin chains, the subcellular localisation of both proteins was first analyzed by co-immunofluorescence experiments (n=7). From day 6 of culture, Hsp70 and α-globin were co-localised in the cytoplam of β-TM erythroblasts. Features of aggregates were sometimes observed in differentiated, haemoglobinised cells, with one typical picture shown in FIG. 2C. Co-localisation was assessed using the average Pearson's correlation coefficient (PCC). At day 8, an apparent high level of co-localisation between Hsp70 and α-globin was detected, both in β-TM (PCC=0.4±0.13) and in controls (PCC=0.31±0.09). This finding was confirmed by Van Steensel's approach (data not shown). Similar findings were observed in fresh bone marrow experiments from patients and healthy donors (data not shown). To further characterise this co-localisation, a close in situ proximity ligation assay we used (Duolink®), which allows the identification of interacting proteins by fluorescent spots. At day 8, spots we detected in β-TM mature haemoglobinised cells (n=3) but much less so in controls. Additionally, cells containing abundant Hsp70/α-globin complexes were apoptotic (FIG. 3A).

Next, using a yeast two-hybrid system, additional evidence for the biochemical interaction of Hsp70 with the human α-globin chains was provided. In the assays, the entire coding sequence of human Hsp70 was used as bait. Blue diploid transformants could be detected on a high stringency minimal medium, indicating a direct interaction between Hsp70 and the α-globin chains. Similar results were obtained when the β-globin coding sequence was used as prey, indicating that both the α- and β-globin chains could interact with Hsp70 (FIG. 3B). To identify the Hsp70 domains involved in this interaction, we tested the binding of α-globin chains to deletion mutants of Hsp70 that expressed either the Nucleotide Binding Domain (NBD) or the Substrate Binding Domain (SBD) of Hsp70 (FIG. 3B). Interestingly, neither of these two deletion mutants interacted with the α-globin chain, suggesting that the entire structure of Hsp70 is required for the recognition of α-globin. To better characterise this interaction, an in silico study involving molecular modelling, docking and molecular dynamics simulations was performed. The α-globin was docked onto a homology-generated model of $Hsp70^{1-701}$. It was found that α-globin binds to a highly electronegative cavity formed by the NBD, SBD and lid (a C-terminal 10 kDa helical subdomain of the SBD) (FIG. 3C). The resulting $Hsp70^{1-701}$/α-globin complex is stabilised by extensive protein-protein interactions mediated mainly by multiple hydrogen bonds engaging the three structural domains of Hsp70 (data not shown). Thus, the binding of α-globin to Hsp70 crucially modulates the chaperone structure and the interdomains interaction between NBD-lid and NBD-SBD. Altogether, these findings indicate that, in addition to Alpha Haemoglobin Stabilising Protein (AHSP), which stabilises the α-globin chains [9], Hsp70 could act as a novel chaperone of α-globin chains. However, this apparent cytoprotective function of Hsp70 might be detrimental during stages of high haemoglobinisation and globin chain imbalance in β-TM by preventing the nuclear localisation of Hsp70 and, consequently, its function in protecting GATA-1 from cleavage by caspase-3.

Figure 4A:
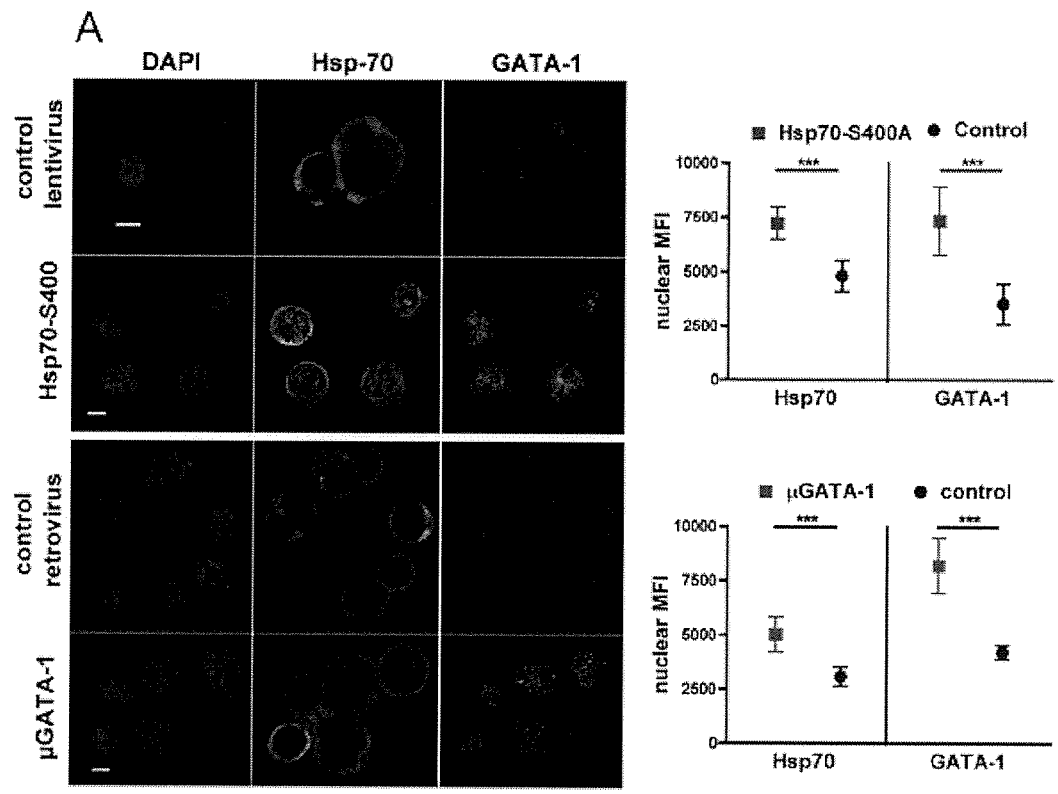
Figure 4B:
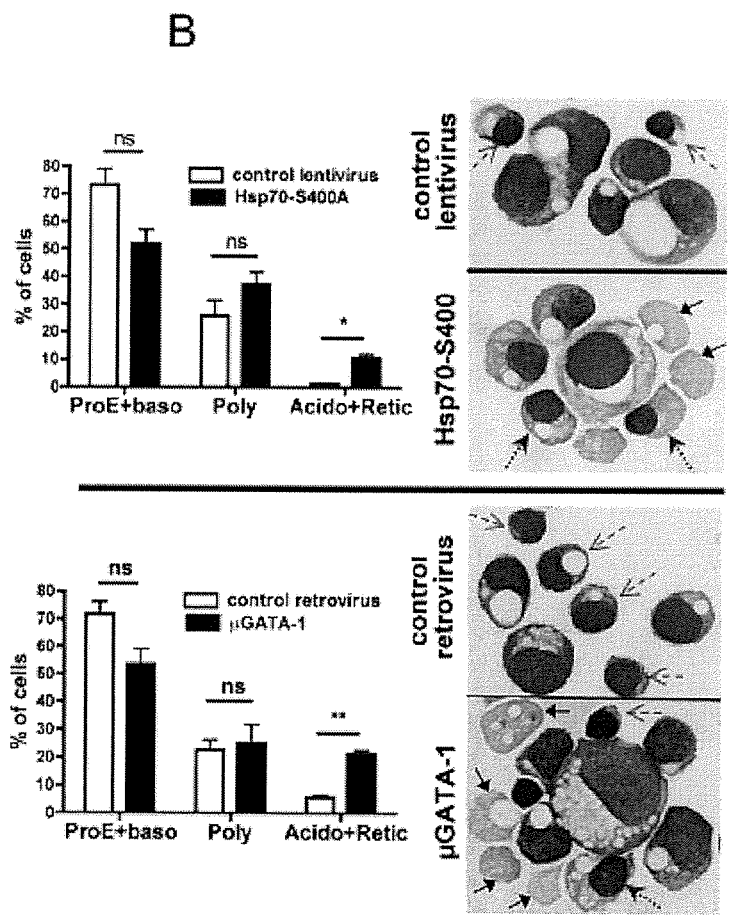

To investigate the contribution of Hsp70 cytoplasmic sequestration to the pathophysiology of β-TM IE, lentiviral transduction we used to restore Hsp70 expression in the nucleus of β-TM erythroblasts. For this purpose, β-TM CD34+ cells (n=3) were transduced with lentiviruses expressing a nuclear-targeted Hsp70 mutant (Hsp70-S400A) [10], wtHsp70, or an empty lentivector. As expected, at day 7 of the differentiation phase of culture, Hsp70-S400A (FIG. 4A) and wtHsp70 (not shown) lentivectors increased nuclear Hsp70 localisation and rescued GATA-1 expression in β-TM erythroid cells. The restoration of nuclear Hsp70 localisation efficiently improved the terminal maturation of β-TM erythroblasts. At day 7, in Hsp70-S400A transduced β-TM erythroblasts, the percentage of mature cells (acidophilic cells and reticulocytes) was increased when compared to the empty vector control (10.6±3.2% vs 1.1±0.7%, p=0.01 FIG. 4B). Similarly, the terminal maturation index was increased (28.1% (IQR 28.1-51.3) vs 4.6% (IQR 1.7-6.7); p=0.01). In addition, rescuing nuclear Hsp70 localisation induced a dramatic two-fold decrease in apoptosis (9.9±2.8% vs 20.7±5.6%; p<0.001) (FIG. 4C). Next, to analyse the consequences of GATA-1 cleavage on the maturation arrest and apoptosis observed in cultured β-TM erythroblasts, we transduced β-TM CD34+ cells with a GATA-1 mutant that was uncleavable by caspase-3 (μGATA-1)[11] or a GFP+ empty vector. The μGATA-1 mutant had a positive effect on erythroid terminal maturation that was similar to that of Hsp70-S400A (FIG. 4A-D). Conversely, apoptosis was not corrected indicating that cleavage of GATA-1 contributes to impair the erythroid maturation but to a less extent to apoptosis of β-TM cells, as previously reported in low grade myelodysplastic syndromes[10].

Figure 6:
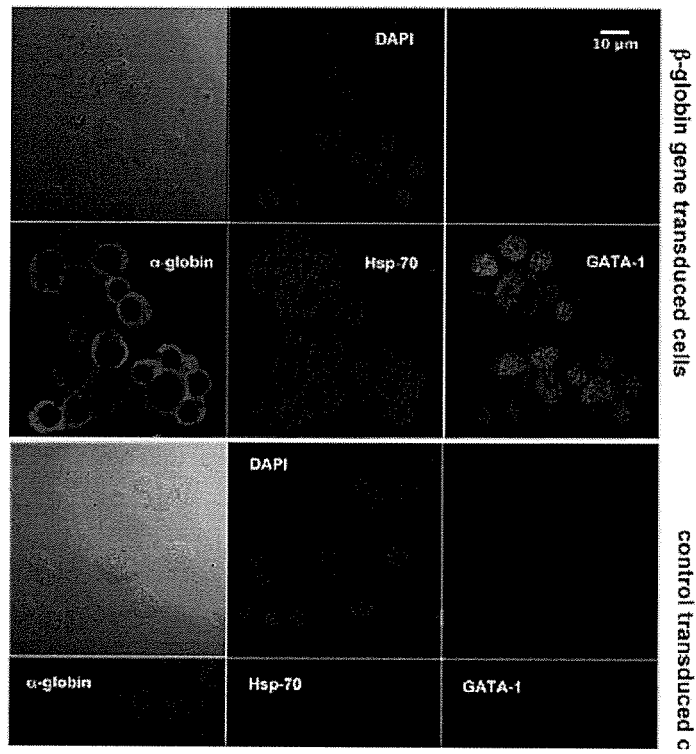
FIG. 6. The lentiviral transduction of β-TM CD34$^+$ cells with the β-globin gene rescues Hsp70 nuclear localisation and GATA-1 protection. β-TM CD34+ cells derived from peripheral blood cells were infected with a lentivirus encoding the β-globin gene or a control virus. They were then cultured with a two-phase amplification liquid culture system, as described. Confocal microscopy analysis at day 8 of the CD36$^+$ cell cultures shows Hsp70 nuclear localisation and GATA-1 expression in β-globin gene transduced cells (top) and control transduced cells (bottom). Scale bar, 10 μm.

Foetal haemoglobin (HbF, $α_2γ_2$), which is replaced after birth by the adult haemoglobin (HbA, $α_2β_2$), is concentrated in a few F cells and represents less than 1% of the haemoglobin content in healthy adults[12]. In β-TM patients, there is an elevation in the proportion of F cells to compensate for the lack of β-chain synthesis, and the only surviving mature erythroblasts are F cells. GATA-1 has a major role in regulating the haemoglobin gene expression; it is sometimes described as a transcription repressor or activator of the human γ-globin chains gene [14-16]. As such, the effect of GATA-1 nuclear restoration on HbF expression was studied by flow cytometry. At day 7, it was observed that while the number of F cells decreased with maturation (data not shown and [17]), the percentage of $HbF^{high}$ cells, as assessed by flow cytometry, was significantly increased concomitantly with the protection of GATA-1 by Hsp70-S400A (54.8%±12 vs 45.9%±10.5; p<0.004) (n=3) and in GATA-1 transduced erythroblasts (51.4±8.2% vs 40.5±9.4%; p<0.002) (n=3) (FIG. 4D). Finally, to ensure the specificity of these findings, β-TM CD34+ cells were lentivirally transduced with the β-globin gene. This led to Hsp70 nuclear re-localisation, GATA-1 protection (FIG. 6), and the restoration of normal erythroid maturation (data not shown).

Taken together, our data demonstrate that the cytoplasmic sequestration of α-globin chains by Hsp70 prevents their nuclear localisation. This is a key mechanism inducing the IE observed in β-TM patients. The modelling studies suggest that Hsp70 could have been selected during evolution to serve as a specific chaperone of globin chains to protect early erythroblasts during erythroid differentiation.

The structural model of the $Hsp70^{1-701}$/α-globin complex provides a new rationale for a targeted therapy in β-thalassemia major IE. Small compounds disrupting the Hsp70/α-globin complex in the cytoplasm may increase the nuclear localisation of Hsp70 and may thus reduce maturation arrest and increase the number of F cells. Ultimately, these outcomes may decrease the patients' requirement for a blood transfusion and the associated complications, including iron overload.

REFERENCES

1. Khandros, E. & Weiss, M. J. Hematology/Oncology Clinics of North America 24, 1071-1088 (2010).
2. Ginzburg, Y. & Rivella, S. Blood 118, 4321-4330 (2011).
3. Yuan, J. et al. Blood 82, 374-377 (1993).
4. Mathias, L. A. et al. Experimental Hematology 28, 1343-1353 (2000).
5. Centis, F. et al. Blood 96, 3624-3629 (2000).
6. Zermati, Y. et al. J Exp Med 193, 247-254 (2001). 11
7. Ribeil, J.-A. et al. Nature 445, 102-105 (2007).
8. Hartl, F. U., Bracher, A. & Hayer-Hartl, M. Nature 475, 324-332 (2011).
9. Kihm, A. J. et al. Nature 417, 758-763 (2002).
10. Frisan, E. et al. Blood 119, 1532-1542 (2012).
11. De Maria, R. et al. Nature 401, 489-493 (1999).
12. Dover, G. J. & Boyer, S. H. Blood 69, 1109-1113 (1987).
13. Yao, X. et al. Exp. Hematol. 37, 889-900 (2009).

14. Woon Kim, Y., Kim, S., Geun Kim, C. & Kim, A. Nucleic Acids Res 39, 6944-6955 (2011).
15. Zhu, J. et al. Blood 117, 3045-3052 (2011).
16. Sankaran, V. G. & Orkin, S. H. Cold Spring Harb Perspect Med 3, (2013).
17. Bhanu, N. V. et al. Blood 105, 387-393 (2005).
18. Zermati, Y. et al. Exp. Hematol. 28, 885-894 (2000).
19. De Franceschi, L. et al. Haematologica 92, 1319-1326 (2007). 26
20. Gabet, A.-S. et al. Cell Death Differ. 18, 678-689 (2011).
21. Schallmeiner, E. et al. Nat. Methods 4, 135-137 (2007).
22. DeLano, W. L. The PyMOL Molecular Graphics System (2002). Website at www.pymol/org
23. R Development Core Team R: A language and environment for statistical computing. (2011). Website at www.R-project.org/
24. Berman, H. M. et al. Nat. Struct. Biol. 7 Suppl, 957-959 (2000).
25. Sousa, R. & Lafer, E. M. Traffic 7, 1596-1603 (2006).
26. Jiang, J. et al. Mol. Cell 28, 422-433 (2007).
27. Wisniewska, M. et al. PLoS ONE 5, e8625 (2010).
28. Gao, X.-C. et al. J. Biol. Chem. 287, 6044-6052 (2012).
29. Larkin, M. A. et al. Clustal W and Clustal X version 2.0. Bioinformatics 23, 2947-2948 (2007).
30. Eswar, N. et al. Nucleic Acids Res. 31, 3375-3380 (2003).
31. Shibayama, N., Sugiyama, K. & Park, S.-Y. J. Biol. Chem. 286, 33661-33668 (2011).
32. Chen, R., Li, L. & Weng, Z. Proteins 52, 80-87 (2003).
33. Mashiach, E. et al. Proteins 78, 3197-3204 (2010).
34. Emekli, U., Schneidman-Duhovny, D., Wolfson, H. J., Nussinov, R. & Haliloglu, T. Proteins 70, 1219-1227 (2008).
35. Brooks, B. R. et al. J Comput Chem 30, 1545-1614 (2009).
36. Van Der Spoel, D. et al. J Comput Chem 26, 1701-1718 (2005).
37. Batcho P F, Case D A & Schlick T Journal of chemical physics 115, 4003-4018 (2001).

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of screening candidate compounds in order to select compounds which inhibit binding of $\alpha$ globin to Hsp70 but which do not inhibit binding of Hsp70 to GATA-1, comprising
   i) providing a plurality of candidate compounds which may inhibit binding of $\alpha$ globin to Hsp70;
   ii) exposing Hsp70 to said plurality of candidate compounds in the presence of $\alpha$ globin and under conditions which allow $\alpha$ globin to bind to Hsp70;
   iii) identifying Hsp-70-compound complexes which do not contain bound $\alpha$ globin;
   iv) exposing Hsp-70-compound complexes identified in said identifying step iii) to GATA-1 under conditions that permit Hsp70 to bind to GATA-1;
   v) identifying Hsp70-compound-GATA-1 complexes fowled in said exposing step iv); and
   vi) selecting compounds identified in said identifying step v) as compounds which inhibit binding of $\alpha$ globin to Hsp70 but which do not inhibit binding of Hsp70 to GATA-1.

2. The method of claim 1, further comprising a step of
   vii) exposing Hsp70-compound-GATA-1 complexes to caspase-1, and
   viii) identifying Hsp70-compound-GATA-1 complexes in which GATA-1 is not cleaved by caspase-1.

* * * * *